United States Patent
Song et al.

(10) Patent No.: US 8,809,226 B2
(45) Date of Patent: Aug. 19, 2014

(54) METHOD OF PRODUCING CARRIER FOR CATALYST FOR OXIDATIVE DEHYDROGENATION OF N-BUTANE, METHOD OF PRODUCING CARRIER-SUPPORTED MAGNESIUM ORTHOVANADATE CATALYST, AND METHOD OF PRODUCING N-BUTENE AND 1, 3-BUTADIENE USING SAID CATALYST

(75) Inventors: In Kyu Song, Seoul (KR); Ho Won Lee, Seoul (KR); Yeon Shick Yoo, Seosan-si (KR); Young Jin Cho, Seosan-si (KR); Jin Suk Lee, Seoul (KR); Ho Sik Jang, Daejeon (KR)

(73) Assignee: Samsung Total Petrochemicals Co., Ltd., Seosan-si, Chungcheongnam-do (KR)

( * ) Notice: Subject to any disclaimer, the term of this patent is extended or adjusted under 35 U.S.C. 154(b) by 189 days.

(21) Appl. No.: 13/415,208

(22) Filed: Mar. 8, 2012

(65) Prior Publication Data

US 2012/0232320 A1 Sep. 13, 2012

(30) Foreign Application Priority Data

Mar. 9, 2011 (KR) .................. 10-2011-0021037
May 30, 2011 (KR) .................. 10-2011-0051293

(51) Int. Cl.

| | | |
|---|---|---|
| B01J 21/04 | (2006.01) | |
| B01J 23/00 | (2006.01) | |
| B01J 23/02 | (2006.01) | |
| B01J 23/04 | (2006.01) | |
| B01J 23/06 | (2006.01) | |
| C01G 27/02 | (2006.01) | |
| C04B 35/48 | (2006.01) | |
| C04B 35/49 | (2006.01) | |
| C07C 5/48 | (2006.01) | |
| C01G 31/00 | (2006.01) | |
| B01J 21/06 | (2006.01) | |
| B01J 23/22 | (2006.01) | |
| B01J 35/00 | (2006.01) | |
| C01G 25/02 | (2006.01) | |
| B01J 37/02 | (2006.01) | |

(52) U.S. Cl.
CPC ............... *C07C 5/48* (2013.01); *C07C 2521/06* (2013.01); *C01G 31/00* (2013.01); *B01J 21/066* (2013.01); *B01J 23/22* (2013.01); *B01J 35/002* (2013.01); *C01G 25/02* (2013.01); *C01P 2006/12* (2013.01); *B01J 37/0201* (2013.01); *C07C 2521/10* (2013.01); *C07C 2523/22* (2013.01); *C01P 2002/72* (2013.01); *Y10S 502/506* (2013.01)
USPC ........... 502/340; 502/349; 502/439; 502/506; 423/608; 501/104

(58) Field of Classification Search
USPC .................. 502/340, 349, 439, 506; 423/608; 501/104
See application file for complete search history.

(56) References Cited

U.S. PATENT DOCUMENTS 3,303,234 A 2/1967 Laimonis
(Continued)

OTHER PUBLICATIONS

"Oxidative dehydration of n-butane to n-butene and 1,3-butadiene over Mg3(VO4)2/MgO-ZrO2 catalysts: Effect of Mg:Zr ratio of support," Jong Kwon Lee et al. Journal of Industrial and Engineering Chemistry 18 (2012; available online Dec. 30, 2011), pp. 1096-1101.*
"Characterization of MgO-ZrO2 precursor powders prepared by in-situ peptisation of coprecipitated oxalate gel," T. Settu. Ceramics International 26 (2000), pp. 517-521.*
(Continued)

*Primary Examiner* — Patricia L Hailey
(74) *Attorney, Agent, or Firm* — Young & Thompson

(57) ABSTRACT

A method of producing a carrier used for a catalyst for oxidative dehydrogenation of n-butane; a method of producing a magnesium orthovanadate catalyst supported by the carrier; and a method of producing n-butene and 1,3-butadiene using the catalyst are described.

5 Claims, 8 Drawing Sheets

(56) References Cited

U.S. PATENT DOCUMENTS

| | | | | |
|---|---|---|---|---|
| 4,605,631 | A | * | 8/1986 | Rossi ................................ 501/1 |
| 4,619,817 | A | * | 10/1986 | Stambaugh et al. .......... 423/266 |
| 6,187,984 | B1 | | 2/2001 | Wu et al. |
| 6,200,680 | B1 | * | 3/2001 | Takeda et al. ................. 428/402 |
| 6,433,241 | B2 | | 8/2002 | Wu et al. |
| 6,592,805 | B1 | * | 7/2003 | Wang et al. ................... 264/614 |
| 2005/0031534 | A1 | * | 2/2005 | Asai .............................. 423/608 |

OTHER PUBLICATIONS

Synthesis and Characterization of Y2O3-ZrO2 and Y2O3-CeO2-ZrO2 Precursor Powders, T. Settu et al. Journal of the European Ceramic Society 16 (1996), pp. 1309-1318.*

"Preparation and Thermal Evolution of Sol-Gel Derived Zirconia and Ceria-Zirconia Precursors," T. Settu et al. Bull. Chem. Soc., Jpn., 67 (1994), pp. 1999-2005.*

* cited by examiner

METHOD OF PRODUCING CARRIER FOR CATALYST FOR OXIDATIVE DEHYDROGENATION OF N-BUTANE, METHOD OF PRODUCING CARRIER-SUPPORTED MAGNESIUM ORTHOVANADATE CATALYST, AND METHOD OF PRODUCING N-BUTENE AND 1, 3-BUTADIENE USING SAID CATALYST

TECHNICAL FIELD

The present invention relates to a method of producing carrier used for a catalyst for oxidative dehydrogenation of n-butane, a method of producing a magnesium orthovanadate (hereinafter, referred as o-vanadate) catalyst supported by thus obtained carrier, and a method of producing n-butene and 1,3-butadiene using said catalyst.

BACKGROUND OF THE INVENTION

With a sharp rise in olefin price in the petrochemical market, the supply of olefins, particularly light olefins which are used as a raw material for various petrochemical products has become an issue in this market. Among those light olefins, demand for and value of n-butene and 1,3-butadiene which serve as a raw material for various synthetic rubber and copolymer products are increasing currently, especially from China, and methods for producing them include naphtha cracking, direct dehydrogenation of n-butane or n-butene, or oxidative dehydrogenation of n-butane or n-butene. Since approximately 90% of n-butene and 1,3-butadiene supplied to the market are produced by naphtha cracking, the operation of a naphtha cracking process has a great influence in the current market. However, a naphtha cracking process, is for the production of basic petrochemical feedstocks such as ethylene, propylene, etc, not a process dedicated to the production of n-butene and 1,3-butadiene, therefore new establishment or expansion of naphtha cracking center only for the purpose of increasing the production of n-butene and 1,3-butadiene is hardly considered, and if so, it would cause further problems of surplus production of other basic petrochemical feedstocks other than n-butene and 1,3-butadiene. Moreover, with an increasing demand for ethylene and propylene, new establishment and operation regarding a naphtha cracking process tends to be rather focused to increase in production yield of ethylene and propylene, and thus modified as a process using light hydrocarbons such as ethane, propane, etc. as a raw material which can result in high production yield for basic petrochemical feedstock such as ethylene, propylene and the like, although its yield for C4 mixtures is low. In addition to that, with the continuous price increase in raw materials for C4 production, the proportion of a process for obtaining C4 in the naphtha cracking process is relatively reduced. In consequence, with those obstacles as above, it is getting more difficult to secure C4 mixtures, particularly n-butene and 1,3-butadiene through a naphtha cracking process.

As the foregoing description, although n-butene and 1,3-butadiene supply majorly depend on a naphtha cracking process, based on the many reasons as above, the naphtha cracking process cannot be an effective way to resolve the imbalance between supply and demand, caused by recent increased demand in n-butene and 1,3-butadiene. In this circumstance, a dehydrogenation reaction in which hydrogens are removed from n-butane or n-butene thus obtaining n-butene and n-butene, is attracting great attention as an alternative process which can rapidly deal with the current changes in market.

Over the past two decades, although many researches in dehydrogenation of n-butane and n-butene, especially n-butene due to its relatively easy process, have been made and reported [H. H. Kung, M. C. Kung, Adv. Catal., vol. 33, p. 159 (1985); J. A. Toledo, P. Bosch, M. A. Valenzuela, A. Montoya, N. Nava, J. Mol. Catal. A, vol. 125, p. 53 (1997); H. Lee, J. C. Jung, H. Kim, Y.-M. Chung, T. J. Kim, S. J. Lee, S.-H. Oh, Y. S. Kim, I. K. Song, Catal. Lett., vol. 131, p. 344 (2009); H. Lee, J. C. Jung, I. K. Song, Catal. Lett., vol. 133, p. 321 (2009); W. Ueda, K. Asakawa, C.-L. Chen, Y. Moro-oka, T. Ikawa, J. Catal., vol. 101, 360等 (1986); R. K. Grasselli, Handbook of Heterogeneous Catalysis, vol. 5, p. 2302 (1997); J. C. Jung, H. Lee, H. Kim, Y.-M. Chung, T. J. Kim, S. J. Lee, S.-H. Oh, Y. S. Kim, I. K. Song, Catal. Lett., vol. 124, p. 262 (2008); J. C. Jung, H. Lee, D. R. Park, J. G. Seo, I. K. Song, Catal. Lett., vol. 131, 401 (2009)], the n-butene price is also sharply rising with rapidly increasing demand from China. Therefore, oxidative dehydrogenation of n-butane is ultimately addressed as an alternative to resolve the current imbalance between n-butene and 1,3-butadiene supply and demand, in petrochemical industry, and thus many related investigations regarding this are being made [N. Kijima, M. Toba, Y. Yoshimura, Catal. Lett., vol. 127, p. 63 (2009); I. C. Marcu, I. Sandulescu, J. M. M. Millet, Appl. Catal. A, vol. 227, p. 309 (2002); L. M. Madeira, J. M. Herrmann, F. G. Freire, M. F. Portela, F. J. Maldonado, Appl. Catal. A, vol. 158, p. 243 (1997); A. A. Lemonidou, G. J. Tjatjopoulos, I. A. Vasalos, Catal. Today, vol. 45, p. 65 (1998)].

The dehydrogenation reaction of n-butane can be classified into direct dehydrogenation and oxidate dehydrogenation, wherein the direct dehydrogenation reaction of n-butane is highly exothermic and thus a thermodynamically disadvantageous reaction since hydrogen should be directly detached from n-butane as well as requires great energy consumption to satisfy the high-temperature reaction condition. For carrying out direct dehydrogenation, used are precious metal catalysts such as platinum or palladium, which require a reactivation process owing to their short lifetime in most cases, therefore the direct dehydrogenation is not a suitable commercial process for producing 1,3-butadiene [A. Wu, C. A. Frake, U.S. Pat. No. 6,433,241 B2 (2002); A. Wu, C. A. Frake, U.S. Pat. No. 6,187,984 (2001)]. On the contrary, unlike the direct dehydrogenation, the oxidative dehydrogenation of n-butane, wherein n-butane and oxygen reacts to produce n-butene and water, and thus obtained n-butene further reacts with oxygen to produce 1,3-butadiene and water, is thermodynamically advantageous since an endothermic reaction turns to an exothermic reaction with the generation of water from the use of oxygen, and rapid temperature changes in catalyst layer which can caused by the heat from the catalyst reaction can be prevented by water generated after the reaction. In this respect, the oxidative dehydrogenation process of n-butane can produce n-butene and 1,3-butadiene through an independent process unlike a naphtha cracking process and be operated under process conditions more advantageous than those of the direct dehydrogenation process. Therefore, when a catalyst process for producing n-butene and 1,3-butadiene with high efficiency is developed, this process can be used as an effective alternative to prior processes to produce n-butene and 1,3-butadiene through an independent energy-saving process.

As described above, the oxidative dehydrogenation of n-butane for producing n-butene and 1,3-butadiene includes a reaction between n-butane and oxygen to produce water and n-butene which reacts with oxygen in the same way again to produce water and 1,3-butadiene. From the above description, although this reaction has many advantages as a commercial process, over the direct dehydrogenation of n-butane in many ways such as a thermodynamic aspect which makes possible to produce n-butene and 1,3-butadiene with a high yield, under mild reaction conditions, it has a drawback that many side reactions such as highly oxidative reactions which involve generation of carbon monoxide or carbon dioxide owing to the use of oxygen as a reactant.

Therefore, the most crucial technical point in the oxidative dehydrogenation process of n-butane is to achieve a catalyst with highly increased selectivity to n-butene and 1,3-butadiene by preventing side reactions such as complete-oxidative reactions, while achieving the conversion of n-butane to the maximum. Although the reaction mechanism of the oxidative dehydrogenation of n-butane has not yet been exactly known, it is reported that, as a first step, solid acid-lattice oxygen cuts the C—H bond of n-butane, which simultaneously causes a redox reaction of a catalyst and loss of lattice oxygen, and therefore complex oxide catalysts containing transition metal ions which may be in various oxidation states are essential to this oxidative dehydrogenation reaction [H. H. Kung, Ind. Eng. Chem. Prod. Res. Dev., vol. 25, p. 171 (1986)].

So far, catalysts known to effectively produce n-butene and 1,3-butadiene through oxidative dehydrogenation of n-butane are magnesium orthovanadate catalysts [M. A. Chaar, D. Partel, H. H. Kung, J. Catal., vol. 105, p. 483 (1987); M. A. Chaar, D. Partel, H. H. Kung, J. Catal., vol. 109, p. 463 (1988); O. S. Owen, H. H. Kung, J. Mol. Catal., vol. 79, p. 265 (1993); A. A. Lemonidou, G. J. Tjatjopoulos, I. A. Vasalos, Catal. Today, vol. 45, p. 65 (1998); Korean patent application No. 10-2011-0021037 (2011) by Song In Kyu, Lee Ho Won, You Yoen Sik, Jo Young Jin, Lee Jin Suck, Jang Ho Sik]; vanadium oxide catalysts [A. F. Dickason, U.S. Pat. No. 3,914,332 (1975); M. E. Harlin, V. M. Niemi, A. O. I. Krause, J. Catal. Vol. 195, p. 67 (2000); V. M. Murgia, E. M. F. Torres, J. C. Gottifredi, E. L. Sham, Appl. Catal. A, vol. 312, p. 134 (2006)]; pyrophosphate catalysts [I. C. Marcu, I. Sandulescu, J. M. M. Millet, Appl. Catal. A, vol. 227, p. 309 (2002); F. Urlan, I. C. Marcu, I. Sandulescu, Catal. Commun., vol. 9, p. 2403 (2008)]; ferrite catalysts [H. Armendariz, J. A. Toledo, G. Aguilar-Rios, M. A. Valenzuela, P. Salas, A. Cabral, H. Jimenez, I. Schifter, J. Mol. Catal., vol. 92, p. 325 (1994); L. Bajars, L. J. Croce, U.S. Pat. No. 3,303,234 (1967)] and the like.

The characteristic feature shared by the above complex oxide catalysts is the presence of transition metals, which are necessary for transition of electrons between the catalyst and n-butane via the redox reaction of the catalyst as explained above [H. H. Kung, Ind. Eng. Chem. Prod. Res. Dev., vol. 25, p. 171 (1986)]. The catalysts can carry out the oxidative dehydrogenation of n-butane by incorporating metals which can be oxidized and reduced such as, for example, vanadium, iron, nickel and titanium, etc, and among them, particularly, magnesium o-vanadate catalysts which contain vanadium are known to have high activity, based on which it is considered for the redox potential of vanadium metal to be suitable for the oxidative dehydrogenation of n-butane [M. A. Chaar, D. Partel, H. H. Kung, J. Catal., vol. 105, p. 483 (1987); M. A. Chaar, D. Partel, H. H. Kung, J. Catal., vol. 109, p. 463 (1988)].

The above-described magnesium o-vanadate catalysts having a chemical formula of $Mg_3(VO_4)_2$ in a rhombic crystalline form, bind with magnesia in the oxidative dehydrogenation of n-butane to be reduced to, optionally via $Mg_2VO_4$ having isometric crystalline structure in the state of vanadium tetraoxide depending on the reaction conditions, $MgV_2O_4$ that is in the form of vanadium trioxide and oxygen [N. Kijima, M. Toba, Y. Yoshimura, Catal. Lett., vol. 127, p. 63 (2009)], wherein the reduction process is carried out by receiving electrons generated from the breakage of C—H bond in n-butane. The reduction of the central metal, vanadium ion from pentoxide to trioxide state is the essential element of the oxidative dehydrogenation of n-butane, and the magnesium o-vanadate catalysts can carry out a redox reaction with n-butane via such oxidation state changes of vanadium and thus be served as catalysts for oxidative dehydrogenation to produce n-butene and 1,3-butadiene from n-butane [N. Kijima, M. Toba, Y. Yoshimura, Catal. Lett., vol. 127, p. 63 (2009)].

Magnesium o-vanadate catalysts are generally produced to be the form in which the active phase of $Mg_3(VO_4)_2$ is supported by a separate metal oxide. It is reported that when magnesium o-vanadate catalysts are not supported, the activity is lower than that of supported magnesium o-vanadate.

For example, some results of oxidative dehydrogenation of n-butane by using unsupported magnesium o-vanadate catalysts have been reported in conventional patents and literatures, specifically, for example, 11.5% of n-butane conversion rate, 6.7% of dehydrogenation product yield under the conditions of 540° C. and the feed composition ratio of n-butane:oxygen:helium=4:8:88[O. S. Owen, H. H. Kung, J. Mol. Catal., vol. 79, p. 265 (1993)], and 5.7% dehydrogenation product yield under the conditions of 540° C. and the feed composition ratio of n-butane:oxygen:helium=5:10:85[A. A. Lemonidou, G. J. Tjatjopoulos, I. A. Vasalos, Catal. Today, vol. 45, p. 65 (1998)]. When magnesium o-vanadate catalysts are supported, the activity can be more improved [A. A. Lemonidou, G. J. Tjatjopoulos, I. A. Vasalos, Catal. Today, vol. 45, p. 65 (1998)]. Specifically, magnesia supported magnesium o-vanadate catalysts obtained by supporting vanadium to excessive amount of magnesia and their excellent activity for the oxidative dehydrogenation of n-butane have been generally reported [M. A. Chaar, D. Partel, H. H. Kung, J. Catal., vol. 109, p. 463 (1988); O. S. Owen, H. H. Kung, J. Mol. Catal., vol. 79, p. 265 (1993); A. A. Lemonidou, G. J. Tjatjopoulos, I. A. Vasalos, Catal. Today, vol. 45, p. 65 (1998)]. Specifically, it was reported that when the oxidative dehydrogenation of n-butane under the conditions of 600° C. and the composition ratio of n-butane:oxygen:nitrogen of 2:1:97 was conducted by using a magnesia-supported magnesium o-vanadate catalyst obtained by mixing magnesium hydroxide with a mixed aqueous solution of ammonium vanadate and ammonia with the ratio of Mg to V of 6:1, it resulted in 30.4% of n-butane conversion rate, 70.6% of dehydrogenation product selectivity and 21.5% of dehydrogenation product yield [N. Kijima, M. Toba, Y. Yoshimura, Catal. Lett., vol. 127, p. 63 (2009)], and when the oxidative dehydrogenation of n-butane under the conditions of 540° C. and the composition ratio of n-butane:oxygen:helium of 5:10:85 was conducted by using a magnesia-supported magnesium o-vanadate catalyst, it resulted in the yield of 22.8% [A. A. Lemonidou, G. J. Tjatjopoulos, I. A. Vasalos, Catal. Today, vol. 45, p. 65 (1998)]. Further, also reported were the results of 35.4% of n-butane conversion rate and 18.1% of dehydrogenation product yield, by using a magnesia-supported magnesium o-vanadate catalyst under the higher oxygen conditions wherein the composition ratio of n-butane:oxygen:helium=5:20:75, as compared to said reactions of the prior arts [J. M. Lopez Nieto, A. Dejoz, M. J. Vazquez, W. O'Leary, J. Cunnungham, Catal. Today, vol. 40, p. 215 (1998)].

Further reported was a method for using magnesium o-vanadate catalyst which makes possible to increase the activity for the oxidative dehydrogenation of n-butane by mixing additives to magnesia-supported magnesium o-vanadate catalyst so as to obtain products from the dehydrogenation, n-butene and 1,3-butadiene with high yield in the literature of [D. Bhattacharyya, S. K. Bej, M. S. Rao, Appl. Catal. A, vol. 87, p. 29 (1992)], wherein the dehydrogenation was carried out under the conditions of 570° C., a composition ratio of n-butane:oxygen:nitrogen of 4:8:88 by using 25 wt % of a magnesia-supported magnesium o-vanadate catalyst further mixed with titanium oxide and chromium oxide, resulting in 54.0% of n-butane conversion rate and 33.8% of dehydrogenation product yield.

Although it is possible to the desired reaction product n-butene and 1,3-butadiene with a very high yield, by using said magnesia-supported magnesium o-vanadate catalyst in the oxidative dehydrogenation of n-butane, its commercial application is limited. This is because that although the magnesia-supported magnesium o-vanadate catalyst has high activity, the redox reaction of the catalyst which should be reversible is carried out partly irreversible, [N. Kijima, M. Toba, Y. Yoshimura, Catal. Lett., vol. 127, p. 63 (2009)], resulting in the high catalyst activity is not maintained for a long time.

Therefore, there are needs for development of novel catalysts which can maintain the catalyst activity for an extended period without loss of initial catalyst activity.

SUMMARY OF THE INVENTION

Therefore, with a purpose to overcome the limit of magnesia-supported magnesium o-vanadate catalysts of the prior arts, the present inventors have developed a method of producing a zirconia carrier which does not show any catalyst inactivation when applied to the oxidative dehydrogenation of n-butane, by replacing magnesia to zirconium; then produced zirconia-supported magnesium o-vanadate catalyst by a simple process wherein magnesium and vanadium are supported in this order to the above-obtained zirconia carrier; and thus produced n-butene and 1,3-butadiene with high yield through the oxidative dehydrogenation of n-butane by using the above-obtained catalyst. Therefore, one object of the present invention is to provide a method for producing a zirconia carrier for a catalyst for oxidative dehydrogenation of n-butane, which is to support active elements comprised of magnesium o-vanadate and makes possible to prevent the magnesium o-vanadate activity from being decreased upon its application to the oxidative dehydrogenation of n-butane.

Another object of the present invention is to provide a method for producing a zirconia-supported magnesium o-vanadate catalyst, comprising supporting the active component, magnesium o-vanadate to the zirconia carrier obtained by the method for producing a zirconia carrier for catalyst for oxidative dehydrogenation of n-butane according to the present invention.

Still another object of the present invention is to provide a method for producing n-butene and 1,3-butadiene, which can carry out the oxidative dehydrogenation of n-butane in more stable way by using the zirconia-supported magnesium o-vanadate catalyst produced by the above method according to the present invention, as compared to a process using a magnesia-supported magnesium o-vanadate catalyst in the prior arts.

Further, the present inventors also have developed a method for producing a magnesia-zirconia complex carrier for a catalyst for the oxidative dehydrogenation which has catalyst activity higher than the zirconia-supported magnesium o-vanadate catalyst while showing no catalyst inactivation when applied to the oxidative dehydrogenation of n-butane. Further, by a simple process of supporting vanadium to thus obtained magnesia-zirconia complex carrier, the present inventors also produced a magnesia-zirconia complex-supported magnesium o-vanadate catalyst which can retain catalyst stability to the oxidative dehydrogenation of the zirconia-supported magnesium o-vanadate catalyst while having the initial catalyst activity that does not significantly inferior to the initial catalyst activity of the magnesium o-vanadate catalyst of the prior art, and then the present inventors produced n-butene and 1,3-butadiene with high yield through the oxidative dehydrogenation of n-butane, by using the above obtained catalyst of the present invention.

Therefore, still other object of the present invention is to provide a method for producing a magnesia-zirconia complex carrier which is to support active elements comprised of magnesium o-vanadate and makes possible to prevent the magnesium o-vanadate activity from being decreased upon its application to the oxidative dehydrogenation of n-butane, thereby obtaining high activity.

Still other object of the present invention is to provide a method for magnesia-zirconia complex-supported magnesium o-vanadate catalyst, which comprises supporting the active component, magnesium o-vanadate to the magnesia-zirconia complex carrier obtained by the method for producing a carrier for catalyst for oxidative dehydrogenation of n-butane according to the present invention.

Still other object of the present invention is to provide a method of preparing n-butene and 1,3-butadiene with high yield through oxidative dehydrogenation of n-butane, which can retain the process stability as much as the zirconia-supported magnesium o-vanadate catalyst, while having the initial catalyst activity that does not significantly fall behind the initial catalyst activity of the magnesium o-vanadate catalyst of the prior arts, by using a catalyst in which magnesium o-vanadate is supported by a magnesia-zirconia complex carrier produced by the method of the present invention.

DETAILED DESCRIPTION OF THE INVENTION

The present invention provides a method for preparing a zirconia carrier for a catalyst for oxidative dehydrogenation of n-butane comprising the following steps:
(a) preparing each alcohol solution of zirconium and oxalic acid by dissolving the zirconium precursor and oxalic acid into an alcohol, respectively;
(b) synthesizing zirconia by mixing the alcohol solution of zirconium and the alcohol solution of oxalic acid prepared in the above step (a); and
(c) preparing a zirconia carrier for a catalyst for oxidative dehydrogenation of n-butane by separating, drying and heating the solid zirconia from the solution resulted from the above step (b).

As for the zirconium precursor used in the above step (a), any conventionally used zirconium precursor may be used without limitation, however at least one selected from zirconium chloride, zirconium oxynitrate and zirconium oxychloride may be preferably used as a precursor, and particularly zirconium chloride is preferably used.

As for oxalic acid used in the above step (a), any commercially available products on the market may be used without limitation, and for example oxalic acid dihydrate may be preferably used. As for the alcohols used in the above step (a), any alcohols which can dissolve the zirconium precursor and oxalic acid, respectively may be used without limitation, and preferably used may be alcohols such as ethanol, propanol, butanol, 2-butanol, and particularly preferred is ethanol.

The zirconium precursor and oxalic acid dissolved in an alcohol, respectively in the above step (a) are preferably used at the ratio of 2 mole or more of oxalic acid based on 1 mole of zirconium, since the amount of oxalic acid required for converting all of the zirconium ions to zirconium oxalate is theoretically twice of the zirconium amount. Therefore, although the oxalic acid may be used at the molar ratio more than twice of the amount of zirconium so as to convert all of the zirconium ions to zirconium oxalate, unpredictable parameters such as solvent acidity owing to oxalic acid may become a problem, and thus the molar ratio of oxalic acid to zirconium is preferably 2-5 to 1.

The method for mixing the alcohol solution of zirconium and the alcohol solution of oxalic acid is not particularly limited, however it is preferable that the mixing of each solution is conducted as slowly as possible so that the zirconium oxalate particle can grow uniformly in its size, and the temperature of the mixed solution being stirred is preferably maintained at room temperature. For, example, the alcohol solution of oxalic acid contained in a syringe can be injected to the alcohol solution of zirconium as slowly as possible, for example 1-12 hours, preferably 3-6 hours at room temperature so that zirconia synthesis can be achieved sufficiently, by using a syringe pump of which speed is finely adjusted.

In the step (c), the solution from the step (b) wherein it is stirred for sufficient time is allowed to stand still for a period sufficient for the solid components to be precipitated, then is subjected to a phase separation, wherein precipitated solid components, for example by filtering or centrifugation are separated from an alcohol so as to obtain a solid component sample. Thus obtained solid component sample is dried.

The purpose of drying the solid component sample is to remove alcohol and moisture remained after the separation process of the sample. In this regard, the temperature by which alcohol evaporation is possible is determined as the lower limitation and the temperature by which thermal changes in the sample can be prevented may be determined as the upper limitation, and the time for drying may be limited within the range in which alcohol is expected to be completely removed from the sample. For example, the drying temperature may be determined to be 50-200° C. and preferably 70-120° C., and the drying time is 3-24 hours and preferably 6-12 hours.

And thus dried solid component sample is heated for example in an electric furnace at 350-800° C. and preferably 500-700° C. for 1-12 hours and preferably 3-6 hours to obtain a pure zirconia carrier.

The purpose of heating the dried solid component sample is not only to synthesize zirconia from zirconium oxalate but also to prevent catalyst denaturation during the use of the catalyst supported by the prepared carrier in the oxidative dehydrogenation reaction, taking the reaction temperature of oxidative dehydrogenation into consideration. For example, heating is carried out in an electric furnace at 350-800° C. and preferably 500-700° C. for 1-12 hours and preferably for 3-6 hours, when the heating temperature is less than 350° C. or the heating time is less than 1 hour, zirconia is not sufficiently synthesized from zirconium oxalate, and when the heating temperature is more than 800° C. or the heating time is more than 12 hours, the crystalline phase of zirconia is degenerated so that it might become unsuitable for the use as a carrier, disadvantageously.

The method for preparing a magnesium o-vanadate catalyst supported by the zirconia carrier prepared as the above described method comprises the following steps:

(i) impregnating the zirconia carrier prepared by the above described method with an aqueous magnesium salt solution;

(ii) preparing magnesium oxide supported by zirconia by heating the product obtained from the above step (i);

(iii) impregnating the zirconia-supported magnesium oxide obtained from the above step (ii) with an aqueous vanadate solution; and (iv) preparing a zirconia-supported magnesium o-vanadate catalyst by heating the product obtained from the above step (iii).

As for the magnesium salt and vanadate used in the method for preparing a catalyst of the present invention, any conventional salts comprising magnesium and vanadate, respectively may be used, for example, magnesium nitrate and ammonium metavanadate may be preferably used without being limited to these, and other conventional magnesium salts and vanadate may be further used depending on the purposes. When using magnesium nitrate and ammonium metavanadate, the nitrate ions and the ammonium ions escape during the impregnation, drying and heating processes, and thus it is possible to minimize the effect of each ions, thereby being suitably used as a magnesium salt and vanadate to be supported to zirconia.

The aqueous magnesium salt solution may be prepared by dissolving magnesium salts into distilled water, and the aqueous vanadate solution may be prepared by dissolving vanadate into an aqueous oxalic acid solution or an ammonium hydroxide solution. In the aqueous solution of each magnesium salt and vanadate, the amount of water may be enough if it can dissolve the salt, and preferably water is used at the minimum as long as it can dissolve the salt sufficiently.

The heating process in the above step (ii) and (iv) is carried out at 350-800° C., preferably at 500-700° C., for 1-12 hours, preferably for 3-6 hours. When the heating temperature is less than 350° C. and the heating time is less than 1 hour, magnesium oxide (magnesia) or magnesium vanadate is not sufficiently synthesized, and when the heating temperature is more than 800° C. or the heating time is more than 12 hours, there is a risk for zirconia to be degenerated, thereby being disadvantageous.

The zirconia-supported magnesium o-vanadate catalyst of the present invention, prepared as above overcome the drawbacks of the conventional magnesia-supported magnesium o-vanadate catalyst for oxidative dehydrogenation, wherein re-oxidation of magnesium o-vanadate which was once reduced during oxidative dehydrogenation of n-butane is suppressed, by using zirconia prepared by the specific method of the present invention as a carrier, thereby achieving the catalyst yield in stable way.

Further, by the carrier of the present invention, it is possible to achieve higher activity than that of a vanadium oxide catalyst supported by other carrier or unsupported magnesium o-vanadate catalyst; the zirconia carrier has no problem in its processability; and it can be directly applied to oxidative dehydrogenation of n-butane without requiring a separate activation step under the reaction conditions, thereby being directly applied to commercial processes.

Further, the present invention provides a method for preparing a magnesia-zirconia complex carrier for a catalyst for oxidative dehydrogenation of n-butane, characterized by comprising the following steps:

(a) preparing each alcohol solution of zirconium and oxalic acid by dissolving the zirconium precursor and oxalic acid into an alcohol, respectively;

(b) synthesizing zirconia by mixing the alcohol solution of zirconium and the alcohol solution of oxalic acid prepared in the above step (a);

(c) obtaining zirconia used for the preparation of a magnesia-zirconia complex carrier by separating, drying and heating the solid component zirconia from the solution resulted from the above step (b);

(d) impregnating zirconia obtained from the above step (c) with an aqueous magnesium salt solution; and (e) obtaining a magnesia-zirconia complex carrier for a catalyst for oxidative dehydrogenation of n-butane by drying and heating the product resulted from the above step (d).

Since the steps (a) to (c) are identical with the steps (a) to (c) of the method for preparing a zirconia carrier, the description regarding the steps (a) to (c) are omitted herein.

As for the magnesium salt used in the step (d) for preparing a magnesia-zirconia complex carrier by forming magnesia on the pure zirconia obtained from the step (c), any conventional salts comprising magnesium may be used, and magnesium salts of which anions can be removed during the course of impregnation, drying and heating process are preferred so as to minimize the effect of ions contained in the salts. For example, magnesium nitrate may be preferably used as such magnesium salt for obtaining magnesia-zirconia complex carrier by being supported to zirconia. Although the amount of magnesium salt for preparing a magnesia-zirconia complex carrier in the step (d) may be determined without any specific limitation, however it is preferred to use 1.5 mole or more of magnesium per 1 mole of vanadium in the final product, magnesium o-vanadate catalyst supported by the magnesia-zirconia complex carrier based on the chemical formula of magnesium o-vanadate wherein the molar ratio of magnesium to vanadium is 1.5, meaning that at least 1.5 times of magnesium amount is theoretically required to form a magnesium o-vanadate. More preferably, 3 to 7 moles of magnesium salt are used per 1 mole of vanadium to be supported, wherein the lower limitation value is determined based on the reason that some amount of magnesium should be remained after the formation of a magnesium o-vanadate catalyst so as to maintain the magnesia in the form of a magnesia-zirconia complex carrier, and the upper limitation value is determined based on the reason that an excessive amount of magnesium will make the ratio of zirconia in the magnesia-zirconia complex carrier too small, thereby having an adverse effect on the catalyst stability.

In the step (d), the composition ratio of magnesia and zirconia forming the magnesia-zirconia complex carrier is not specifically limited, however in order to prepare a carrier for a magnesium o-vanadate catalyst which can achieve the purpose of the present invention to maintain the great initial activity for a long time in a stable way, the molar ratio of magnesia:zirconia is preferably in the range of about 0.5-16:1 and still preferably about 0.5-4:1.

In the above step (d), the aqueous magnesium salt solution may be prepared by dissolving the magnesium salt into distilled water and then used for impregnation, wherein the amount of water is preferably used at the minimum, i.e. the amount just enough to dissolve the magnesium salt.

In the above step (e), the product resulted from the step (d) is dried, and the dried solid sample is heated to obtain a magnesia-zirconia complex carrier for oxidative dehydrogenation. The drying process in the step (e) is to remove the moisture remained after the impregnation of magnesium salt to zirconia, wherein the temperature and time for drying may be determined according to the general drying conditions in the art, for example the drying temperature may be 50-200° C., preferably 70-120° C., and the drying time may be 3-24 hours and preferably 6-12 hours.

Further, the heating process in the above step (e) is carried out, for example, at the temperature in the range of 350-800° C. and preferably 500-700° C., for 1-12 hours and preferably 3-6 hours, wherein when the temperature is less than 350° C. or the time is less than 1 hour, the magnesia synthesis may not be sufficiently conducted, and when the temperature is more than 800° C. or the time is more than 12 hours, zirconia can be degenerated, disadvantageously.

The method for preparing a magnesium o-vanadate catalyst supported by the magnesia-zirconia complex carrier according to the present invention, using the magnesia-zirconia complex carrier prepared as the above described method, comprises the following steps:

(i) impregnating the magnesia-zirconia complex carrier prepared by the above-described method with an aqueous vanadate solution; and (ii) preparing a magnesium o-vanadate catalyst supported by a magnesia-zirconia complex carrier by drying and heating the product obtained from the above step (i).

As for the vanadate used in the method for preparing a catalyst of the present invention, any conventional vanadate may be used without any limitation, for example, ammonium metavanadate may be preferably used without limitation, and other conventional vanadate may be further used depending on the purposes. When using ammonium metavanadate as a vanadate, the ammonium ions escape during the impregnation, drying and heating processes, and thus it is possible to minimize the effect of each ions, thereby being suitably used as a vanadate to be supported to the magnesia-zirconia complex carrier.

The aqueous vanadate solution may be prepared by dissolving vanadate into an aqueous oxalic acid solution or an ammonium hydroxide solution. In the aqueous solution, the amount of water may be enough if it can dissolve the salt, and preferably water is used at the minimum as long as it can dissolve the salt sufficiently.

When dissolving the vanadate, as for the oxalic acid or an ammonium hydroxide solution for helping dissolution of the vanadate, any commercially available products on the market may be used without limitation, for example oxalic acid dehydrate may used preferably.

The drying process in the step (ii) is to remove the moisture remained after the impregnation of vanadate, wherein the temperature and time for drying may be determined according to the general drying conditions in the art, for example the drying temperature may be 50-200° C., preferably 70-120° C., and the drying time may be 3-24 hours and preferably 6-12 hours.

Further, the heating process in the above step (ii) is carried out to remove oxalic acid which is used to dissolve and impregnate vanadate, and to synthesize magnesium o-vanadate supported from the vanadate supported by the magnesia-zirconia complex carrier. For example, it is carried out at the temperature in the range of 350-800° C. and preferably 500-700° C., for 1-12 hours and preferably 3-6 hours, wherein when the temperature is less than 350° C. or the time is less than 1 hour, the magnesia o-vanadate synthesis may not be sufficiently conducted, and when the temperature is more than 800° C. or the time is more than 12 hours, the crystalline structure of zirconia in the magnesia-zirconia complex carrier can be degenerated, disadvantageously.

The magnesium o-vanadate catalyst supported by the magnesia-zirconia complex carrier of the present invention as prepared by the above-described method, by using magnesia-zirconia prepared by the specific method of the present invention as a carrier, in order to overcome the drawbacks of the conventional magnesia-supported magnesium o-vanadate catalyst for oxidative dehydrogenation of n-butane, suppresses re-oxidation of magnesium o-vanadate which was once reduced during oxidative dehydrogenation of n-butane, thereby achieving the catalyst yield in stable way as well as high catalyst activity as compared to the zirconia-supported magnesium o-vanadate catalyst of the prior art. Additionally, it does not have any problem in the processability of the magnesia-zirconia complex carrier, and it can be directly applied to oxidative dehydrogenation of n-butane without requiring a separate activation step under the reaction conditions, thereby being directly applied to commercial processes.

Further, the present invention is to provide a method for preparing n-butene and 1,3-butadiene which comprises carrying out oxidative dehydrogenation of n-butane on the magnesium o-vanadate catalyst supported by the zirconia carrier or magnesia-zirconia complex carrier prepared by the above-described method. The reactant for the oxidative dehydrogenation of n-butane is a mixed gas comprising n-butane, oxygen and nitrogen, at the ratio by volume of n-butane:oxygen:nitrogen=2-10:0.5-40:50-97.5, preferably n-butane:oxygen:nitrogen=4:2-20:76-94, more preferably 4:2-10:86-94. When the volume ratio of n-butane, oxygen and nitrogen is out of said range, a side reaction, i.e. complete oxidation during the oxidative dehydrogenation of n-butane occurs greatly; the catalyst activity becomes lowered and process safety is not good, disadvantageously.

When feeding the reactant in the form of a mixed gas to a reactor, the amount of the reactant being fed which may be adjusted by a mass flow meter controller is adjusted to be preferably 50-5000 $h^{-1}$, preferably 500-3000 $h^{-1}$, more preferably 1000-2000 $h^{-1}$ of Gas hourly space velocity (GHSV) based on the amount of n-butane. When the space velocity is less than 50 $h^{-1}$, the catalyst reaction is localized to a limited section, leading to coking of the side products from the catalyst reaction, or heat emitted during the reaction may cause a hot spot, disadvantageously, and when the speed is more than 5000 $h^{-1}$, the catalyst reaction cannot sufficiently occur in the reactant passing the catalyst bed, disadvantageously.

The temperature for carrying out the oxidative dehydrogenation of n-butane is preferably maintained at the range of 300-800° C., more preferably 450-600° C., and most preferably 500° C. When the reaction temperature is less than 300° C., n-butane cannot be sufficiently activated, and when it is more than 800° C., decomposition reaction of n-butane occurs, disadvantageously.

INDUSTRIAL AVAILABILITY

According to the present invention, it is possible to obtain a magnesium o-vanadate catalyst based on a zirconia carrier for the oxidative dehydrogenation of n-butane from which n-butene and 1,3-butadiene can be prepared with high production yield in a stable way, by using zirconia which can be easily prepared by a method involving simple components and synthetic processes, and commercially readily available magnesium salt and vanadate. Further, by using the magnesium o-vanadate catalyst based on the zirconia carrier prepared by the present invention to the oxidative dehydrogenation of n-butane, it is possible to overcome the defect of a conventional magnesium o-vanadate catalyst in the prior art, i.e. catalyst inactivation and achieves the reaction in a stable way, thereby being directly applicable to a commercial process, advantageously.

Still further, according to the present invention, it is possible to prepare a magnesia-zirconia complex carrier in which magnesia is formed on the zirconia, by using zirconia which can be easily prepared by a method involving simple components and synthetic processes and commercially readily available magnesium salt, as well as, by applying vanadate to the resulted carrier, a magnesium o-vanadate catalyst based on a magnesia-zirconia complex carrier for the oxidative dehydrogenation of n-butane from which n-butene and 1,3-butadiene can be prepared with high production yield in a stable way.

Further, according to the present invention, by applying a magnesium o-vanadate catalyst supported by the magnesia-zirconia complex carrier prepared by supporting magnesium salt to zirconia prepared by a gel-oxalate method to oxidative dehydrogenation of n-butane, it is possible to overcome the inactivation problem of conventional magnesium o-vanadate in the prior arts, thus obtain high initial catalyst activity in a consistent way, and carry out the reaction in a stable and efficient way, thereby being immediately applied to a commercial process.

Further, according to the present invention, n-butene and 1,3-butadiene for which demand and value are gradually increasing owing to their wide use as intermediates for various petrochemical products in petrochemical industry can be prepared from n-butane which does not have wide applications, thereby being possible to achieve highly added value of C4 petrochemical feedstocks. Additionally, by the present invention, it is possible to ensure a process dedicated to the production of n-butene and 1,3-butadiene without new establishment of additional naphtha crackers, thereby satisfying demand for n-butene and 1,3-butadiene and acquiring economic benefits while actively coping with the market changes in the future.

EXAMPLES

Figure 1:
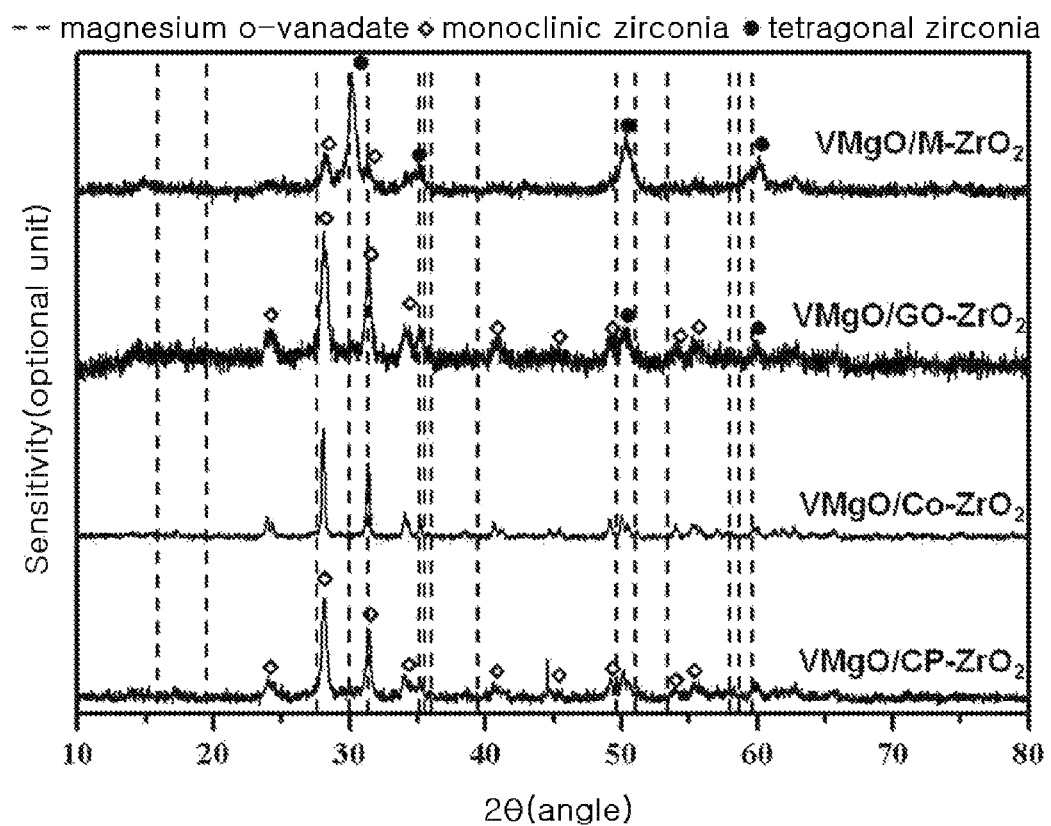
FIG. 1 is a plot representing the results of X-ray diffraction of magnesium o-vanadate catalysts supported by zirconia prepared by various methods according to the preparation example 2 and comparative preparation example 2.

Hereinafter, the present invention is further illustrated in detail via specific examples as given below. However, it should be understood that the following examples are described only for an illustrative purpose, without any intention to limit the scope of the present invention.

Preparation Example 1

Preparation of Zirconia by Gel-Oxalate Method

For the preparation of zirconia, zirconium chloride 9.5 g was dissolved into ethanol (500 ml) to prepare an ethanol solution of zirconium, and oxalic acid dihydrate 12.3 g was dissolved into ethanol (100 ml) to prepare an ethanol solution of oxalic acid. After dissolution is sufficiently achieved in each solution, the ethanol solution of oxalic acid was injected to the ethanol solution of zirconium through a syringe pump as slowly as possible, and the mixture was sufficiently stirred. The mixed solution was again stirred at room temperature for 12 hours by using a magnetic stirrer so as to be sufficiently stirred, and allowed to stand still at room temperature for phase separation. In order to remove unnecessary ions such as chloride from the phase-separated mixed solution, the ethanol solution was filtered and the filtrate was again washed with the ethanol solution and stirred, and this same procedure was conducted several times. Then, the final solution having the precipitates was centrifuged and thus obtained solid sample was dried at 80° C. for 12 hours. Thus prepared solid sample was heated in an electric furnace maintained at 550° C. for 3 hours, thereby obtaining a single phase zirconia prepared by the gel-oxalate method. Thus prepared zirconia was referred as $GO-ZrO_2$.

Preparation Example 2

Preparation of Magnesium O-Vanadate Catalyst Supported by the Zirconia Prepared by the Gel-Oxalate Method By supporting a magnesium salt and vanadate to the prepared zirconia ($GO-ZrO_2$) prepared by the gel-oxalate method according to the above preparation example 1, a magnesium o-vanadate catalyst supported by zirconia was prepared. The preparation method in detail is as follow. 1.7 g magnesium nitrate 6 hydrates was dissolved into a small amount of distilled water, and the resulted solution was mixed with 2.0 g zirconia prepared by the preparation example 1 by impregnation. After drying the magnesium-supporting zirconia at 80° C. for 12 hours, the resulted solid sample was heated in an electric furnace under air atmosphere maintained at 550° C. for 3 hours so that magnesia was formed from the magnesium salt. Next, the obtained magnesia-zirconia sample was impregnated with an aqueous ammonium metavanadate solution which was prepared by dissolving 0.5 g ammonium metavanadate (wherein the atomic ratio of magnesium:vanadium=3:2) into a small amount of an aqueous oxalic acid solution in which 1.06 g oxalic acid was dissolved, dried at 80° C. for 12 hours, and thus obtained solid sample was in an electric furnace under air atmosphere maintained at 550° C. for 3 hours, thereby finally obtaining a magnesium o-vanadate catalyst supported by zirconia. The catalyst prepared by the above process was referred as VMgO/GO—$ZrO_2$ (GO refers to being prepared by gel-oxalate method).

By X-ray diffraction analysis, the phase of the obtained catalyst was observed, and the results were represented in FIG. 1. As seen from FIG. 1, the surface analysis results of the zirconia-supported magnesium o-vanadate catalyst prepared by the preparation example 2 showed that the zirconia prepared by the gel-oxalate method was present as two different phases of monoclinic system zirconia and tetragonal system zirconia which were partially mixed. The characteristic phase of magnesium o-vanadate supported by zirconia was found to be present over a wide range with small intensity, and the small phases widely distributed over the corresponding range were identified, although they were very weak.

The composition ratio and surface area of the zirconia-supported magnesium o-vanadate catalyst prepared by the preparation example 2 of the present invention were investigated by ICP element analysis and BET surface area analysis, and the results were represented in the following Table 1. As seen from Table 1, the composition ratio of the catalyst was found to be close to the calculated value for the catalyst preparation, which suggested the formation of the magnesium o-vanadate catalyst, although it was not confirmed by the X-ray diffraction test results.

TABLE 1

Element composition ratio and BET surface area of zirconia-supported magnesium o-vanadate catalyst prepared by the gel-oxalate method

| Catalyst | Wt % based on $V_2O_5$ | Element composition ratio(MgO:$ZrO_2$) | Element composition ratio(MgO:$V_2O_5$) | BET surface area($m^2$/g) |
|---|---|---|---|---|
| VMgO/ GO-$ZrO_2$ | 14.4% | 0.5:1 (theoretical value = 0.42:1) | 3.7:1 (theoretical value = 3.0:1) | 18.8 |

Comparative Preparation Example 1

Preparation of 3 Species of Zirconia by Various Preparation Methods

For comparison, 3 species of zirconia were prepared by various preparation methods. Firstly, commercially available zirconia (Co—$ZrO_2$) was purchased. Secondly, zirconia was synthesized by dissolving zirconium chloride 9.46 g and ammonium carbonate 9.36 g into 500 ml of distilled water, respectively and mixing the solutions at once, then the synthesized zirconia was stirred, filtered so as to obtain solid sample which was dried and heated in an electric furnace under air atmosphere maintained at 550° C. for 3 hours to obtain a final zirconia product (co-precipitation, CP—$ZrO_2$).

Thirdly, zirconia was prepared by a generally used sol-gel preparation method for zirconia synthesis. Specifically, a mixed solution of 10 g CTAB (Cetyl Trimethyl Ammonium Bromide), 100 ml 2-butanol and 1.6 ml ammonium hydroxide solution at 80° C. was mixed with a solution in which 12 ml zirconium butoxide was dissolved into 100 ml 2-butanol prepared at room temperature and stirred for 3 hours so as to obtain transparent zirconia sol which was reacted at 100° C. for 24 hours to obtain zirconia gel. The zirconia gel was filtered, dried and heated in an electric furnace under air atmosphere maintained at 550° C. for 3 hours to obtain a final zirconia product, meso-porous zirconia (M—$ZrO_2$) by the above-described sol-gel method.

Comparative Preparation Example 2

Preparation of Zirconia-Supported Magnesium O-Vanadate Catalyst by Using Various Methods For comparison, to the various zirconia prepared by the above comparative preparation example 1, magnesium and vanadate were supported by the same method and conditions as in the above preparation example 2, thereby preparing 3 species of zirconia-supported magnesium o-vanadate catalysts. The catalysts prepared therefrom were referred as VMgO/Co—$ZrO_2$ (Co, Commercially purchased zirconia), VMgO/CP—$ZrO_2$ (prepared by Co-Precipitation method (CP)), VMgO/M—$ZrO_2$ (M: Mesoporous Zirconia, prepared by sol-gel method).

The phase of the prepared catalyst was observed by X-ray diffraction analysis, and the results were represented in FIG. 1, together with the result of the catalyst prepared by the preparation example 2. As shown in FIG. 1, from the results of surface analysis of 4 species of zirconia-supported magnesium o-vanadate catalysts prepared by the preparation example 2 and the comparative preparation example 2, respectively, the zirconia phase was shown to be monoclinic system or tetragonal system, or a partial mixture thereof. The characteristic phase of magnesium o-vanadate supported by zirconia was found to be present over a wide range with small intensity, and the small phases widely distributed over the corresponding range were identified, although they were very weak.

Comparative Preparation Example 3

Preparation of Magnesium O-Vanadate Catalyst Supported by Magnesia

For comparison with the zirconia-supported magnesium o-vanadate catalyst according to the present invention, a magnesia-supported magnesium o-vanadate catalyst was prepared by the conventional technique. The specific method for preparing the catalyst was as follows. An amount of ammonium metavanadate was weighed to be 15 wt % based on vanadium pentoxide in the final catalyst, dissolved into an ammonium hydroxide solution and impregnated with 5 g of commercially available magnesia as a carrier for the catalyst. Thus obtained sample was dried at 80° C. for 12 hours and the resulted solid sample was heated in an electric furnace under air atmosphere maintained at 550° C. for 3 hours so as to form a magnesia-supported magnesium o-vanadate catalyst by the reaction between magnesium oxide and vanadium ions. The resulted catalyst was referred as VMgO/MgO.

Figure 2:
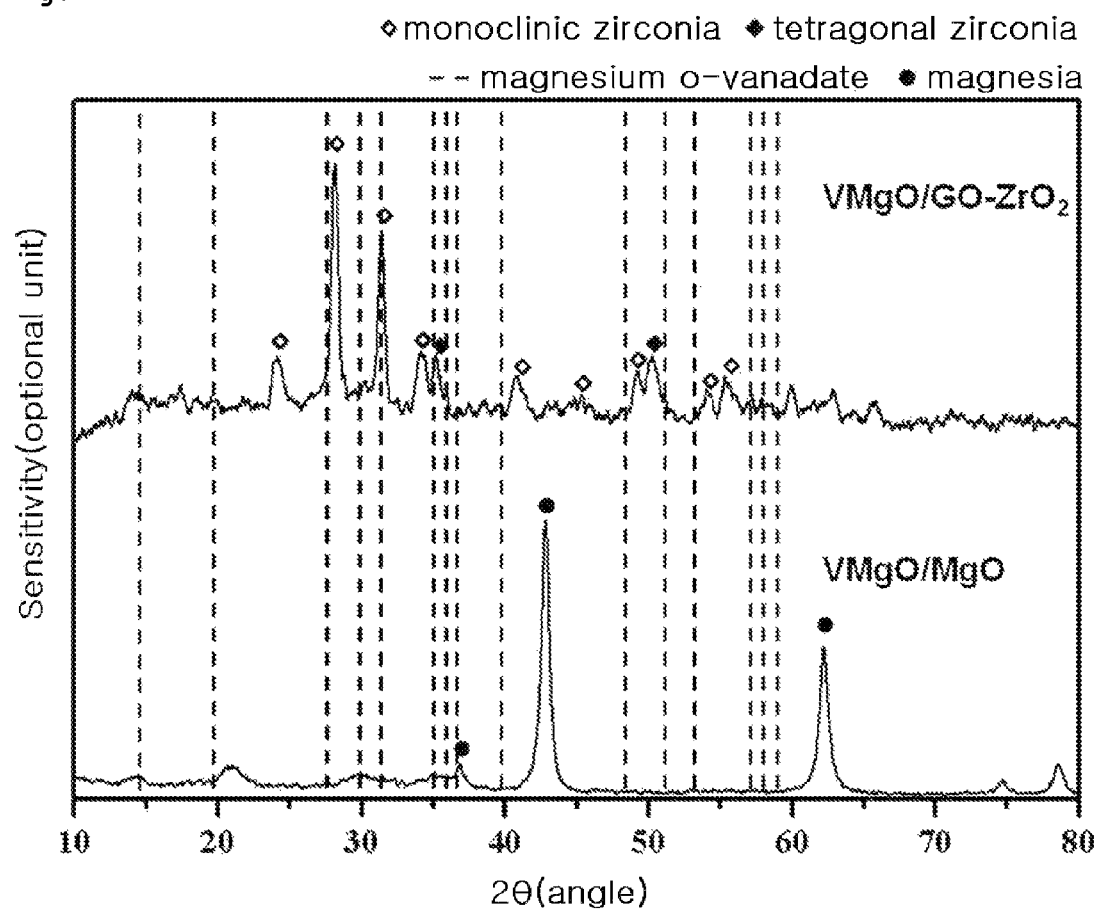
FIG. 2 is a plot representing the results of X-ray diffraction of a magnesium o-vanadate catalyst supported by zirconia prepared by the preparation example 2 and a magnesium o-vanadate catalyst supported by magnesia prepared by the conventional technique, the comparative preparation example 3.

The X-ray diffraction analysis results of the zirconia-supported magnesium o-vanadate catalyst according to the preparation example 2 of the present invention and the magnesia-supported magnesium o-vanadate catalyst according to the comparative preparation example 3 of the present invention were represented in FIG. 2. Similar to FIG. 1, from the results, the characteristic phases of the carrier, zirconia and magnesia were clearly observed, however the characteristic phase of the active element of the catalyst, i.e. magnesium o-vanadate was not observed since it had a small intensity and was generally distributed over a wide range.

Therefore, in order to confirm the formation of a magnesium o-vanadate catalyst, an element analysis by using ICP was carried out by comparing the element composition ratio measured by ICP of the zirconia-supported magnesium o-vanadate catalyst prepared according to the preparation example 2. Further, BET surface analysis was conducted in order to observe the surface area of the catalyst. The ICP element analysis results and BET surface area analysis results were represented in Table 2, together with the results obtained from the zirconia-supported magnesium o-vanadate catalyst prepared according to the preparation example 2 for comparison. From the results in which the supported amount of V, although it was less than the calculated value, was closed to the calculated theoretical value approximately, and V-containing phase was not particularly found from the X-ray diffraction analysis, it was determined that magnesium o-vanadate was formed without specific difficulty, although it could not be clearly observed owing to the unique phase property characterized by the small X-ray diffraction patterns.

TABLE 2

Element composition ratio and BET surface area of the magnesia-supported magnesium o-vanadate catalyst and zirconia-supported magnesium o-vanadate catalyst prepared by the gel-oxalate method

| Catalyst | Wt % based on $V_2O_5$ | Element composition ratio(MgO:$ZrO_2$) | Element composition ratio(MgO:$V_2O_5$) | BET surface area($m^2$/g) |
|---|---|---|---|---|
| VMgO/ GO-$ZrO_2$ | 14.4% | 0.5:1 (theoretical value = 0.42:1) | 3.7:1 (theoretical value = 3.0:1) | 18.8 |
| VMgO/ MgO | 14.2% | 1:0 (theoretical value = 1:0) | 26.8:1 (theoretical value = 23.7:1) | 78.9 |

Example 1

Oxidative Dehydrogenation of N-Butane by Using Continuous Flow Type Catalyst Reactor The oxidative dehydrogenation of n-butane was carried out by using the zirconia-supported magnesium o-vanadate catalyst prepared by the gel-oxalate method according to the preparation example 2 under the conditions as described below.

The reactant for the oxidative dehydrogenation of n-butane in this example 1 was a C4 mixture containing 99.4 wt % of n-butane, and the specific composition thereof was represented in the following table 3.

TABLE 3

Composition of C4 mixture used as a reactant

| Composition | Molecular formula | Wt % |
|---|---|---|
| i-butane | $C_4H_{10}$ | 0.18 |
| n-butane | $C_4H_{10}$ | 99.40 |
| 1-butene | $C_4H_8$ | 0.34 |
| cis-2-butene | $C_4H_8$ | 0.08 |
| Total | | 100.00 |

The C4 mixture as a reactant was fed in the form of a mixed gas with oxygen and nitrogen.

The composition ratio of the reactant was determined based on the amount of n-butane in the C4 mixture, to be n-butane:oxygen:nitrogen of 4:6:90 by volume.

The reaction was carried out by fixing the catalyst powder in a cylindrical pirex reactor for the catalyst reaction, maintaining the reaction temperature of the catalyst bed by placing the reactor in an electric furnace, and letting the reactant continuously passed the catalyst bed inside the reactor thereby proceeding with the reaction.

The amount of catalyst was set to achieve the feeding speed of the reactant to be 2000 $h^{-1}$ based on n-butane. Before flowing the reactant, the temperature of the reactor with the fixed bed was maintained at 520° C. for 1 hour, while flowing nitrogen and oxygen for catalyst activation, and the reaction temperature, i.e. the temperature of the catalyst bed of the fixed bed reactor was maintained at 500° C. Since the product obtained from the reaction contained carbon dioxide from complete oxidation, side products from cracking, other side products for example from an isomerization reaction and unreacted n-butane, other than the main products n-butene and 1,3-butadiene, gas chromatography was used to separate and analyze them. The n-butane conversion rate, the selectivity to dehydrogenation products and yield of the oxidative dehydrogenation of n-butane carried out on the zirconia- or magnesia-supported magnesium o-vanadate catalyst were calculated by the following equation 1, 2 and 3.

$$\text{conversion rate (\%)} = \frac{\text{mole number of reacted n-butane}}{\text{mole number of fed n-butane}} \times 100 \quad [\text{Equation 1}]$$

$$\text{selectivity (\%)} = \frac{\text{mole number of the resulted dehydrogenation product}}{\text{mole number of the reacted n-butane}} \times 100 \quad [\text{Equation 2}]$$

$$\text{Yield (\%)} = \frac{\text{mole number of the resulted dehydration product}}{\text{mole number of n-butane fed}} \times 100 \quad [\text{Equation 3}]$$

The results of the oxidative dehydrogenation of n-butane carried out on the zirconia-supported magnesium o-vanadate catalyst prepared by the gel-oxalate method according to the preparation example 2 were represented in the following Table 4 and FIG. 3.

TABLE 4

Activity of the zirconia-supported magnesium o-vanadate catalyst prepared by the gel-oxalate method

| Catalyst | n-butane conversion rate(%) | Selectivity to products in dehydrogenation(%) | Product yield in dehydrogenation(%) |
|---|---|---|---|
| VMgO/GO-ZrO$_2$ | 27.8 | 44.3 | 12.3 |

Comparative Example 1

Activity of Various Zirconia-Supported Magnesium O-Vanadate Catalyst to the Oxidative Dehydrogenation For comparing the activity of the zirconia-supported magnesium o-vanadate catalyst to the oxidative dehydrogenation prepared by the gel-oxalate method according to Example 1, the oxidative dehydrogenation of n-butane was carried out as in the method described in Example 1 by using a zirconia-supported magnesium o-vanadate catalysts prepared by the various methods according to the comparative preparation example 2. Further, for investigating the effect of the zirconia preparation conditions, i.e. the effect of zirconia prepared by a method other than the gel-oxalate method, on the resulted magnesium o-vanadate supported thereto, the oxidative dehydrogenation results of Example 1 and Comparative example 1, respectively were compared and represented in the following Table 5 and FIG. 3.

Figure 3:
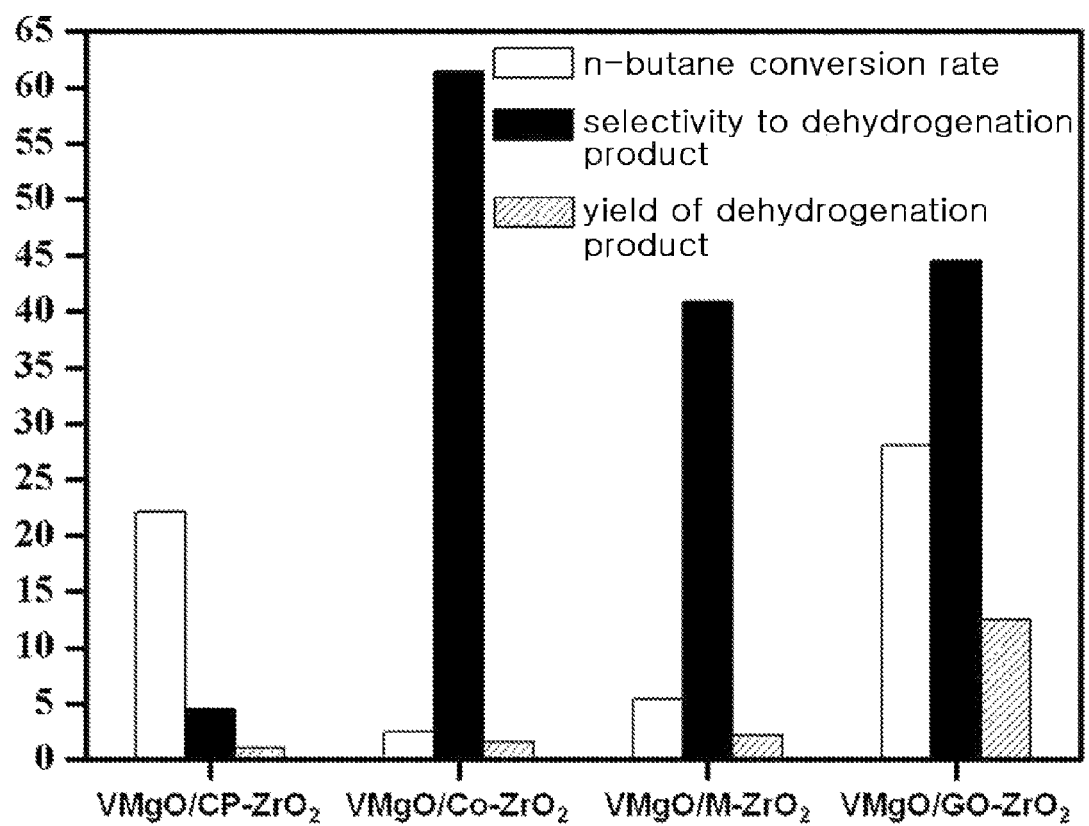
FIG. 3 is a plot representing the differences in catalyst activity over oxidative dehydrogenation of n-butane between the zirconia-supported magnesium o-vanadate catalysts prepared by the preparation example 2 and the comparative preparation example 2.

As seen from Table 5 and FIG. 3, the catalyst prepared by supporting magnesium o-vanadate to zirconia prepared by gel-oxalate showed considerably higher activity than the catalyst in which magnesium o-vanadate was supported to commercially purchased zirconia, zirconia prepared by coprecipitation or mesoporous zirconia prepared by the sol-gel method, in the catalyst activity, thereby having the potential as one and only catalyst being applicable to oxidative dehydrogenation of n-butane among the 4 species of catalysts. Although the mechanism of oxidative dehydrogenation of n-butane by a magnesium o-vanadate catalyst was not clearly known, it has been reported that generally in case of hydrocarbons, particularly paraffin such as n-butane in oxidative dehydrogenation, the acid-base characteristics of the catalyst surface is very important [H. H. Kung, Ind. Eng. Chem. Prod. Res. Dev., vol. 25, p. 171 (1986)]. Therefore, it can be determined that zirconia prepared by the gel-oxalate method is the one having suitable acid-base characteristics as a carrier for being used in the oxidative dehydrogenation of n-butane. Further, from the fact that catalyst inactivation occurs in some zirconia-based catalysts prepared by other methods, it is further assumed that zirconia preparation conditions could affect not only the acid-base properties of a catalyst but also oxidation-reduction of magnesium o-vanadate catalyst. Accordingly, it has come to the present inventors' mind that, for providing zirconia-supported magnesium o-vanadate catalyst, a the method for preparing zirconia as a carrier suitable for the oxidative dehydrogenation of n-butane can be still another object of the present invention

TABLE 5

Activity of 4 species of supported magnesium o-vanadate catalysts based on zirconia prepared by various methods

| Catalyst | Conversion rate of n-butane(%) | Selectivity to dehydrogenation product(%) | Yield of dehydrogenation product(%) |
|---|---|---|---|
| VMgO/CP—ZrO$_2$ | 22.1 | 4.5 | 1.0 |
| VMgO/Co—ZrO$_2$ | 2.5 | 61.4 | 1.6 |
| VMgO/SG-ZrO$_2$ | 5.4 | 40.9 | 2.2 |
| VMgO/GO-ZrO$_2$ | 27.8 | 44.3 | 12.3 |

Comparative Example 2

Oxidative Dehydrogenation by Magnesia-Supported Magnesium O-Vanadate Catalyst

Figure 4:
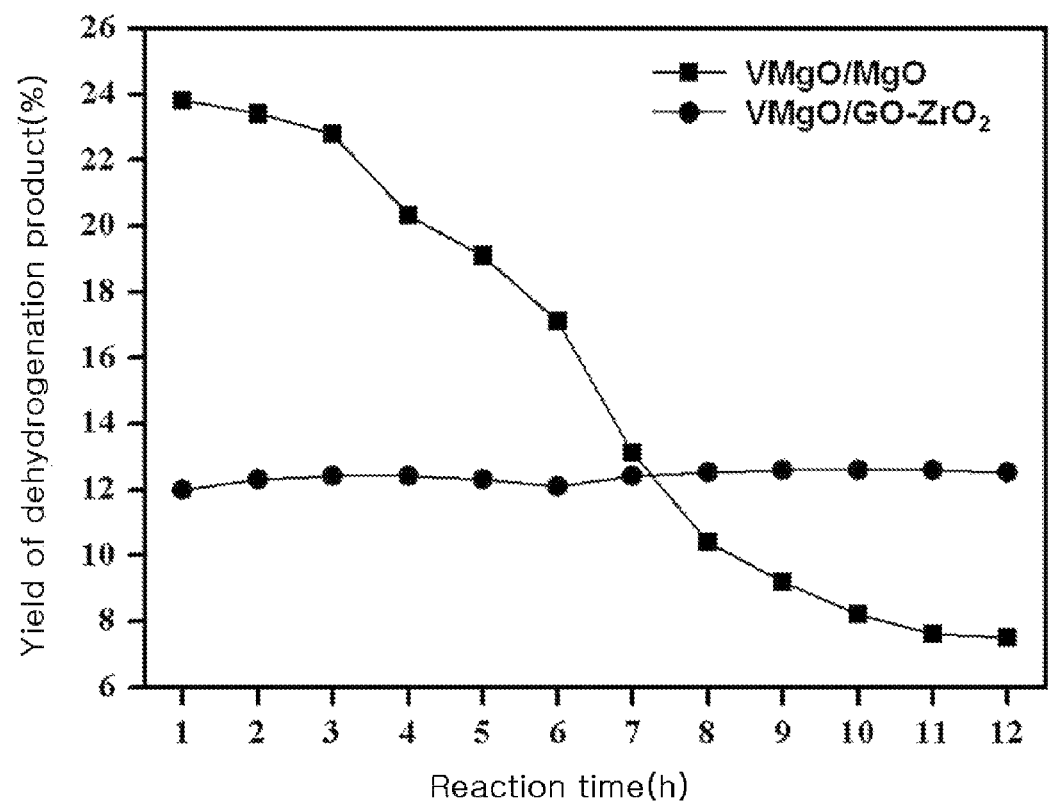
FIG. 4 is a plot representing the catalyst activity changes over time and differences thereof in oxidative dehydrogenation of n-butane between the zirconia-supported magnesium o-vanadate catalysts prepared by the preparation example 2 and the magnesia-supported magnesium o-vanadate catalyst prepared by the conventional technique, the comparative preparation example 3.

For comparing the zirconia-supported magnesium o-vanadate catalyst prepared by the gel-oxalate according to the present invention with a conventional magnesia-supported magnesium o-vanadate catalyst, the oxidative dehydrogenation of n-butane was carried out as in the method described in Example 1 by using a magnesia-supported magnesium o-vanadate catalyst prepared by the conventional methods according to the comparative preparation example 3, and the results therefrom were represented by Table 6 and FIG. 4.

As described before, since the magnesia carrier cannot solve the irreversible oxidation-reduction problem, i.e. generation of the magnesium o-vanadate phase during the oxidative dehydrogenation, such inactivation appeared little by little. Therefore, the test for the comparative example 2 was conducted by observing the progress of activity over time, and as seen from Table 6 and FIG. 4, which represent the results of oxidative dehydrogenation of n-butane for 12 hours, the magnesia-based magnesium o-vanadate catalyst could not maintain the high initial activity and represented a rapid decrease in activity from 3 hours after the reaction. From the fact that the carbon content on the catalyst before and after the reaction was not changed, it was assumed that such catalyst inactivation was not by coking, and the decrease in catalyst activity to oxidative dehydrogenation of n-butane which essentially required oxidation-reduction of a catalyst was rather by the increase of the vanadium species which could not be re-oxidized after catalyst reduction.

On the contrary, the test results of the magnesium o-vanadate catalyst based on zirconia prepared by the gel-oxalate method according to Example 1 as represented in the following Table 6 and FIG. 4, did not show inactivation during the catalyst reaction unlike the results from the comparative example 2. It was assumed that such stability of the catalyst having a zirconia carrier was obtained from the zirconia carrier prepared by the gel-oxalate which helped the re-oxidation of the active species, i.e. magnesium o-vanadate. Therefore, by the zirconia-based magnesium o-vanadate catalyst prepared by the gel-oxalate method according to the present invention, it is possible to obtain the dehydrogenation product with a high yield as compared to the conventional vanadium-type catalysts as well as to overcome the catalyst inactivation problem in the conventional magnesia-based magnesium o-vanadate catalyst and the filtrate was again washed with the ethanol solution and stirred, and this same procedure was conducted several times. Then, the final solution having the precipitates was centrifuged and thus obtained solid sample was dried at 80° C. for 12 hours. Thus prepared solid sample was heated in an electric furnace maintained at 550° C. under air atmosphere for 3 hours, thereby obtaining a single phase zirconia prepared by the gel-oxalate method.

Preparation Example 4

Preparation of 3 Species of Magnesia-Zirconia Complex Carrier by Supporting Magnesium Salt A magnesium salt was supported to the zirconia prepared by the gel-oxalate according to the above preparation example 3, thereby obtaining 3 species of magnesia-zirconia complex carriers at the ratio of magnesia:zirconia being 4:1, 2:1 and 1:1, respectively. The specific preparation method was as follows.

For obtaining 3 g magnesia-zirconia complex carrier, 4.7 g, 7.5 g and 10.8 g magnesium nitrate 6 hydrates were dissolved into a small amount of distilled water, and each resulted aqueous solution was mixed with 2.3 g, 1.8 g and 1.3 g zirconia prepared by the above preparation example 1, respectively in this order, by using a general initial impregnation method. The magnesium supported by zirconia sample was dried at 80° C. for 12 hours, and thus obtained solid sample was heated in an electric furnace maintained at 550° C. under air atmosphere for 3 hours, thereby forming magnesia from the magnesium salt.

Preparation Example 5

Preparation of 3 Species of Magnesium O-Vanadate Catalyst Supported by a Magnesia-Zirconia Complex Carrier

TABLE 6

Activity changes over time of the conventional magnesia-supported magnesium o-vanadate catalyst prepared by the gel-oxalate method

| catalyst | Yield of the dehydrogenation product (%) | Yield of the dehydrogenation product (%) | | | | | | | | | | | |
|---|---|---|---|---|---|---|---|---|---|---|---|---|---|
| | | Time (h) | | | | | | | | | | | |
| | | 1 | 2 | 3 | 4 | 5 | 6 | 7 | 8 | 9 | 10 | 11 | 12 |
| VMgO/GO—ZrO$_2$ | | 12.0 | 12.3 | 12.4 | 12.4 | 12.3 | 12.1 | 12.4 | 12.5 | 12.6 | 12.6 | 12.6 | 12.5 |
| VMgO/MgO | | 23.8 | 23.4 | 22.8 | 20.3 | 19.1 | 17.1 | 13.1 | 10.4 | 9.2 | 8.2 | 7.6 | 7.5 |

Preparation Example 3

Preparation of Zirconia by Gel-Oxalate Method

For the preparation of 10 g of zirconia, zirconium chloride 18.9 g was dissolved into ethanol (1000 ml) to prepare an ethanol solution of zirconium, and at the same time, oxalic acid dihydrate 24.6 g was dissolved into ethanol (200 ml) to prepare an ethanol solution of oxalic acid. After dissolution is sufficiently achieved in each solution, the ethanol solution of oxalic acid was injected to the ethanol solution of zirconium through a syringe pump as slowly as possible, and the mixture was sufficiently stirred. The mixed solution was again stirred at room temperature for 3 hours by using a magnetic stirrer so as to be sufficiently stirred, and allowed to stand still at room temperature for 12 hours for phase separation. In order to remove unnecessary ions such as chloride from the phase-separated mixed solution, the ethanol solution was filtered 0.74 g of ammonium vanadate was dissolved into and impregnated with an aqueous oxalic acid solution wherein 1.6 g of oxalic acid was dissolved so as to make the standard amount of supported vanadium pentoxide be 16 wt % in 3 g of magnesia-zirconia complex carrier prepared by the preparation example 4. The resulted solution was dried at 80° C. for 12 hours, and thus obtained solid sample was heated in an electric furnace under air atmosphere maintained at 550° C. for 3 hours so as to form a magnesium o-vanadate catalyst supported by the magnesia-zirconia complex carrier. The resulted catalysts were referred as VMgO/MgZrO$_4$, VMgO/MgZrO$_2$, VMgO/MgZrO$_1$, depending on the magnesia:zirconia molar ratio of 4:1, 2:1 and 1:1, respectively.

Figure 5:
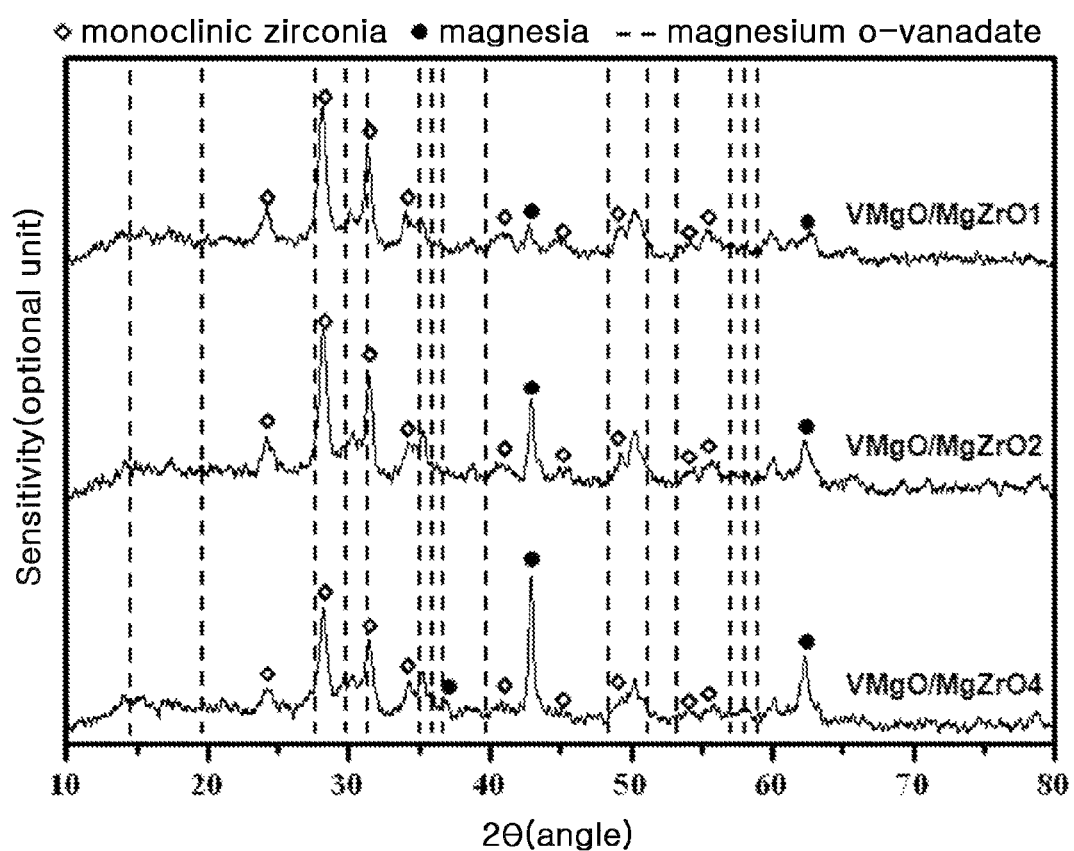
FIG. 5 is a plot representing the results of X-ray diffraction of the magnesium o-vanadate catalyst supported by the magnesia-zirconia complex carrier prepared by the preparation examples 3, 4 and 5 according to the present invention.

By X-ray diffraction analysis, the phase of the obtained catalyst was observed, and the results were represented in FIG. 5. As seen from FIG. 5, from the surface analysis results of the magnesium o-vanadate catalysts supported by magnesia-zirconia complex carrier prepared by the preparation examples 3, 4 and 5, it was supposed that the characteristic small peaks of magnesium o-vanadate are developed a little over the carrier wherein two phases of monoclinic system zirconia and magnesia are mixed. The characteristic phases of the monoclinic system zirconia or magnesia were developed very well and thus clearly observed, however the characteristic phase of the magnesium o-vanadate was not clearly found since it had very small intensity and was generally distributed over a very wide range.

The composition ratio and surface area of the magnesium o-vanadate catalyst supported by the magnesia-zirconia complex carrier prepared by the preparation examples 3, 4 and 5 of the present invention were investigated by ICP element analysis and BET surface area analysis, and the results were represented in the following Table 7. As seen from Table 7, the composition ratio of the catalyst was found to be close to the calculated value for the catalyst preparation, which suggested the formation of the magnesium o-vanadate catalyst, although it was not confirmed by the X-ray diffraction test results.

TABLE 7

Element composition ratio and BET surface area of a magnesium o-vanadate catalyst supported by the magnesia-zirconia complex carrier

| Catalyst | $V_2O_5$ based wt % | Element composition ratio($MgO:ZrO_2$) | Element composition ratio($MgO:V_2O_5$) | BET surface area ($m^2/g$) |
|---|---|---|---|---|
| VMgO/ MgZrO4 | 16.1% | 3.8:1 (theoretical value = 4:1) | 13.1:1 (theoretical value = 3.0:1) | 34.8 |
| VMgO/ MgZrO2 | 16.1% | 2.1:1 (theoretical value = 2:1) | 9.5:1 (theoretical value = 3.0:1) | 34.6 |
| VMgO/ MgZrO1 | 16.0% | 1.1:1 (theoretical value = 1:1) | 6.3:1 (theoretical value = 3.0:1) | 35.0 |

Comparative Preparation Example 4

Preparation of Magnesia-Supported Magnesium O-Vanadate Catalyst

For comparison with the magnesia-zirconia-supported magnesium o-vanadate catalyst according to the present invention, magnesia-supported magnesium o-vanadate catalyst was prepared by the conventional technique. The specific method for preparing the catalyst was as follows.

0.74 g of ammonium metavanadate, was weighed so as to be 16 wt % based on vanadium pentoxide in the final catalyst, dissolved into an ammonium hydroxide solution and impregnated with 3 g of commercially available magnesia as a carrier for the catalyst. Thus obtained sample was dried at 80° C. for 12 hours and the resulted solid sample was heated in an electric furnace under air atmosphere maintained at 550° C. for 3 hours so as to form a magnesia-supported magnesium o-vanadate catalyst by the reaction between magnesium oxide and vanadium ions. The resulted catalyst was referred as VMgO/MgO.

Figure 6:
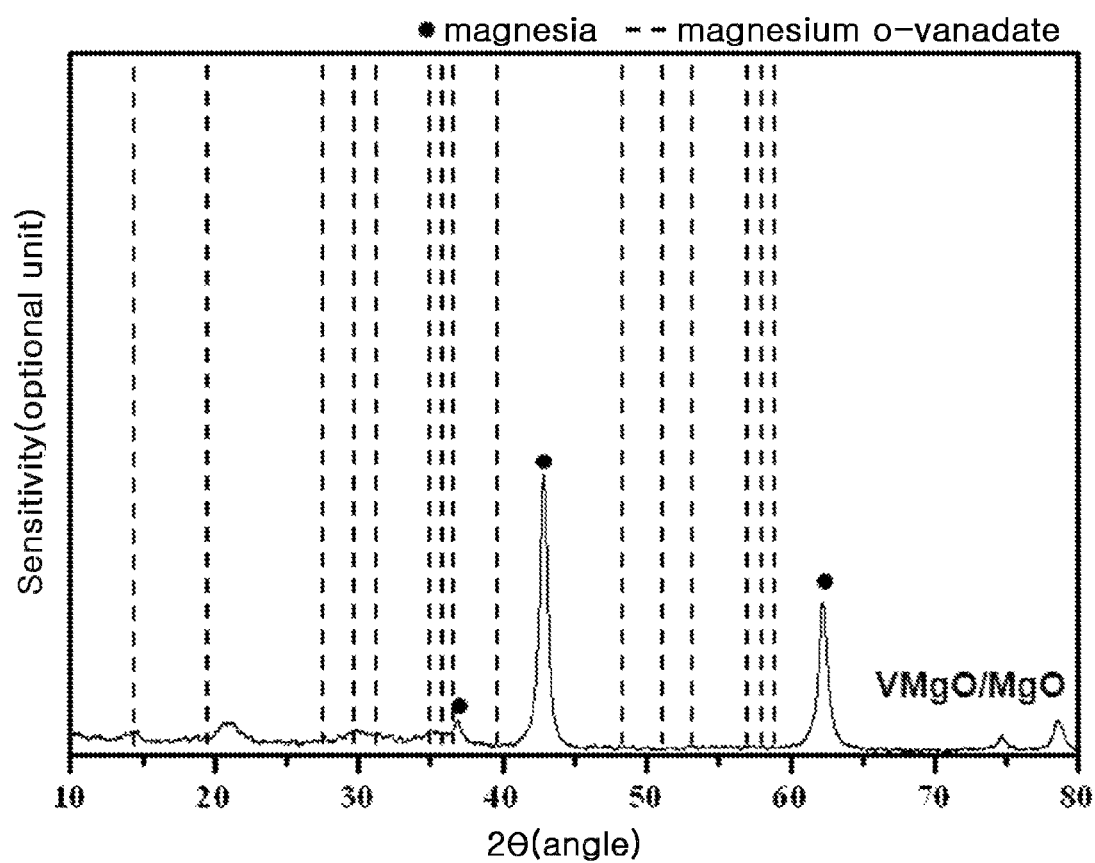
FIG. 6 is a plot representing the results of X-ray diffraction of the magnesia-supported magnesium o-vanadate catalyst prepared by the conventional technique, the comparative example 4.

The X-ray diffraction analysis results of the magnesia-supported magnesium o-vanadate catalyst according to this comparative preparation example 4 of the present invention were represented in FIG. 6. Similar to FIG. 5, from the results, the characteristic phase of the carrier, magnesia was clearly observed, however the characteristic phase of the active element of the catalyst, i.e. magnesium o-vanadate was not observed since it had a small intensity and was generally distributed over a wide range.

The composition ratio and surface area of the zirconia-supported magnesium o-vanadate catalyst according to the preparation example 2 and the magnesia-supported magnesium o-vanadate catalyst according to the comparative preparation example 4 were confirmed by ICP element analysis and BET surface area analysis, and the results were represented in Table 8.

From the catalyst element composition ratio results as represented in Table 8, it was confirmed that the supported amount of V approximated to the calculated theoretical value, and thus it was determined that magnesium o-vanadate was formed without specific difficulty, although a V-containing phase was not particularly observed from the X-ray diffraction analysis, which may be because of the unique phase property characterized by the small X-ray diffraction patterns,

TABLE 8

Element composition ratio and BET surface area of a zirconia-supported magnesium o-vanadate catalyst and a magnesia-suported magnesium o-vanadate catalyst

| Catalyst | $V_2O_5$ based wt % | Element composition ratio($MgO:ZrO_2$) | Element composition ratio($MgO:V_2O_5$) | BET surface area ($m^2/g$) |
|---|---|---|---|---|
| VMgO/ $ZrO_2$ | 16.2% | 0.48:1 (theoretical value = 0.44:1) | 3.2:1 (theoretical value = 3.0:1) | 21.7 |
| VMgO/ MgO | 16.2% | — | 23.3:1 (theoretical value = 23.7:1) | 72.3 |

Example 2

Oxidative Dehydrogenation of N-Butane Through Continuous Flow Catalyst Reactor

The oxidative dehydrogenation of n-butane was carried out by using a magnesium o-vanadate catalyst supported by the magnesia-zirconia complex carrier prepared by the method according to the preparation example 5, and the specific reaction conditions were as follows.

The reactant for the oxidative dehydrogenation of n-butane in this example 2 was a C4 mixture containing 99.4 wt % of n-butane, and the specific composition thereof was represented in the above table 3.

The C4 mixture as a reactant was fed in the form of a mixed gas with oxygen and nitrogen.

The composition ratio of the reactant was determined based on the amount of n-butane in the C4 mixture, to be n-butane:oxygen:nitrogen of 4:8:88 by volume.

The reaction was carried out by fixing the catalyst powder in a straight quartz reactor for the catalyst reaction, maintaining the reaction temperature of the catalyst bed by placing the reactor in an electric furnace, and letting the reactant continuously passed the catalyst bed inside the reactor thereby proceeding with the reaction. The amount of catalyst was set to achieve the feeding speed of the reactant to be 2000 $h^{-1}$ based on n-butane. Before flowing the reactant, the temperature of the reactor with the fixed bed was raised to 500° C. while flowing nitrogen and oxygen for catalyst activation, and the reaction temperature, i.e. the temperature of the catalyst bed of the fixed bed reactor was maintained at 500° C. Since the product obtained from the reaction contained carbon dioxide from complete oxidation, side products from cracking, other side products for example from an isomerization reaction and unreacted n-butane, other than the main products n-butene and 1,3-butadiene, gas chromatography was used to separate and analyze them. The n-butane conversion rate, the selectivity to dehydrogenation products and yield of the oxidative dehydrogenation of n-butane carried out on the zirconia- or magnesia-supported magnesium o-vanadate catalyst were calculated by the equation 1, 2 and 3 as described above in the example 1.

The oxidative dehydrogenation of n-butane was carried out by using magnesium o-vanadate catalysts supported by each 3 species of magnesia-zirconia complex carriers prepared by the above preparation example 5 for 24 hours. The results obtained after 24 hours of the oxidative dehydrogenation were represented in the following Table 9 and FIG. 7, and the activity changes to the reaction over time during 24 hours were represented in FIG. 8.

TABLE 9

Catalyst activity after 24 hours of the oxidative dehydrogenation of 3 species of magnesium o-vanadate catalysts based on the magnesia-zirconia complex carrier

| Catalyst | Conversion rate of n-butane (%) | Selectivity to dehydrogenation product(%) | Yield of dehydrogenation product(%) |
|---|---|---|---|
| VMgO/MgZrO4 | 33.2 | 48.2 | 16.0 |
| VMgO/MgZrO2 | 33.4 | 41.4 | 13.8 |
| VMgO/MgZrO1 | 33.3 | 39.3 | 13.2 |

Figure 7:
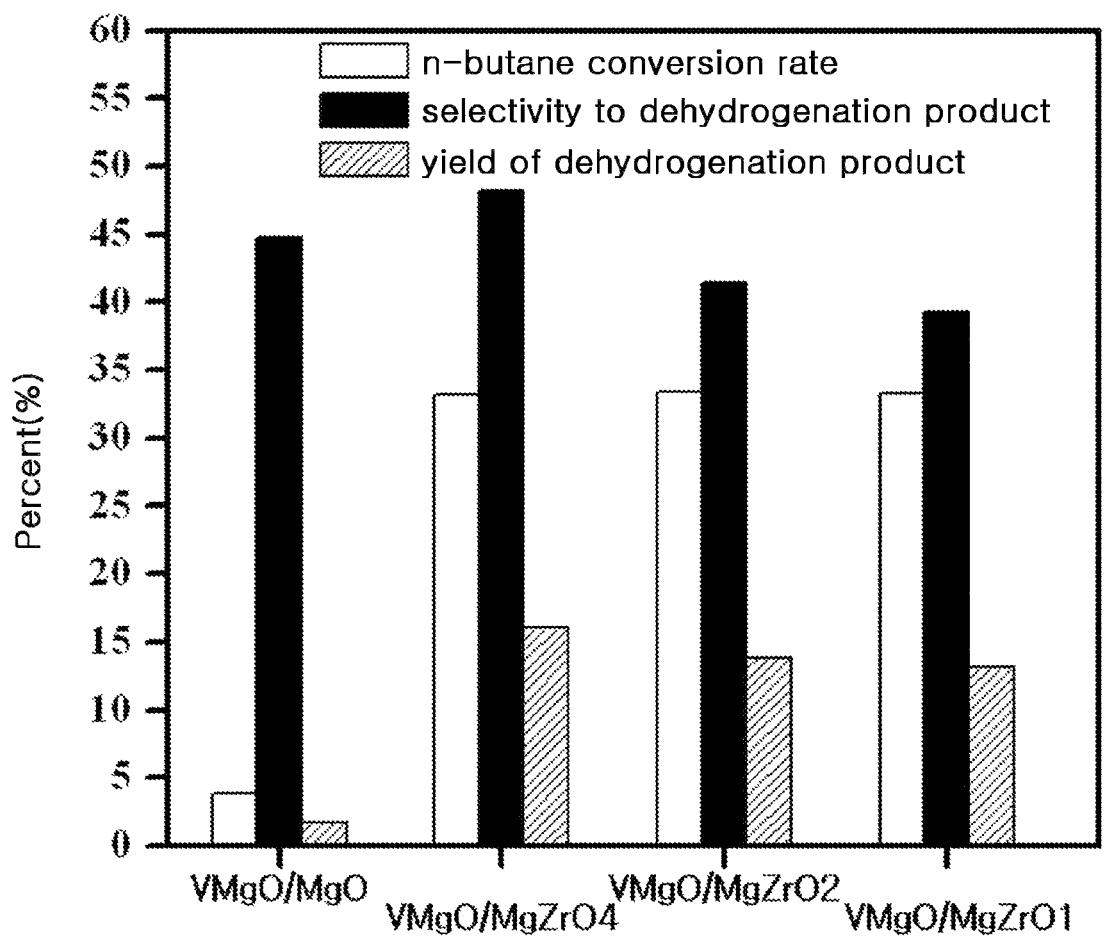
FIG. 7 is a plot representing the differences in the catalyst activity over oxidative dehydrogenation of n-butane for 24 hours, between the magnesium o-vanadate catalyst supported by the magnesia-zirconia complex carrier according to the example 2 of the present invention and the magnesia-supported magnesium o-vanadate catalyst according to comparative example 3 prepared by the conventional technique, the comparative preparation example 3.

As seem from Table 9 and FIG. 7, the magnesium o-vanadate catalyst supported by the mangnesia-zirconia complex carrier showed very high activity in the catalyst activity test, and accordingly the magnesia-zirconia complex carrier was determined to be suitable for a carrier for a catalyst for the oxidative dehydrogenation of n-butane. This is because that the magnesia-zirconia complex carrier takes advantages of each magnesia and zirconia and exerts synergic effects.

The results of the oxidative dehydrogenation carried out by using a magnesia-supported magnesium o-vanadate catalyst according to the following comparative example 3 were also represented in FIG. 7, which were shown to have very low activity.

Comparative Example 3

Oxidative Dehydrogenation Activity of Magnesia-Supported Magnesium O-Vanadate Catalysts For comparing the activity to the oxidative dehydrogenation of the magnesium o-vanadate catalyst supported by the magnesia-zirconia carrier conducted by the example 2 according to the present invention, the oxidative dehydrogenation of n-butane as described in the above example 2 by using the conventional magnesia-supported magnesium o-vanadate catalyst prepared by the above comparative preparation example 4, and the results obtained after 24 hours of the reaction were represented in the following Table 10.

TABLE 10

Catalyst activity on 24 hours after the start of the oxidative dehydrogenation of the magnesia-supported magnesium o-vanadate catalyst

| Catalyst | Conversion rate of n-butane(%) | Selectivity to dehydrogenation product(%) | Yield of dehydrogenation product(%) |
|---|---|---|---|
| VMgO/MgO | 3.8 | 44.7 | 1.7 |

Figure 8:
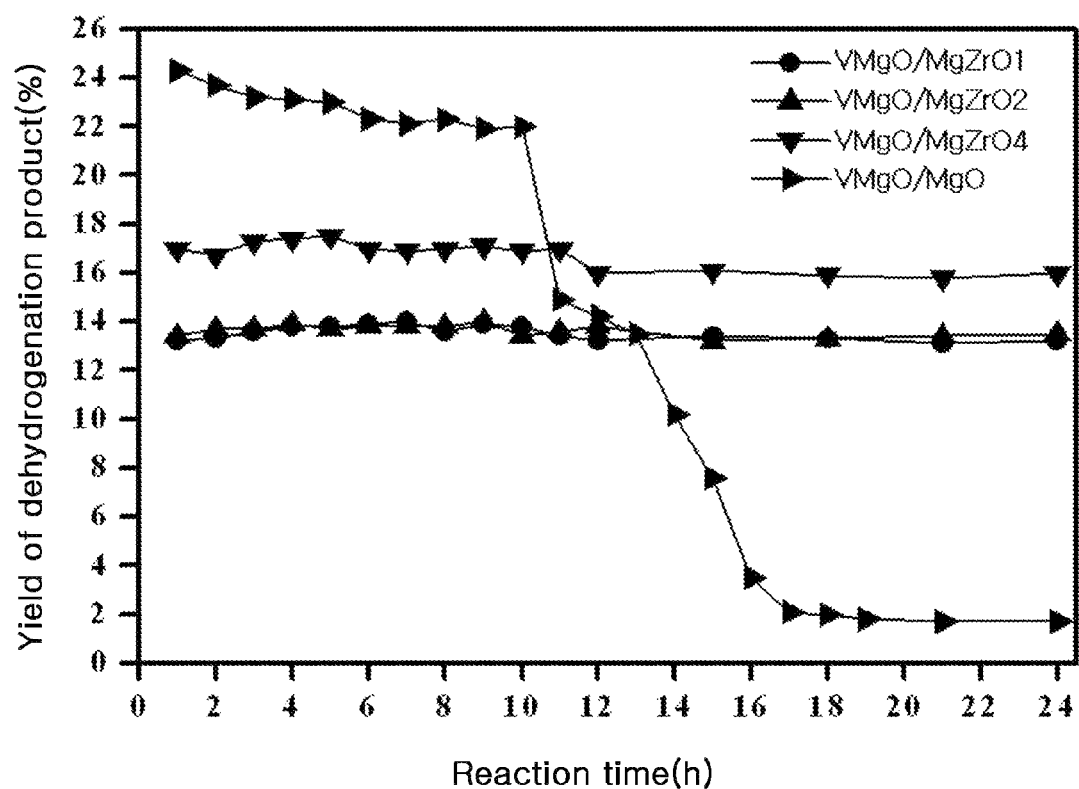
FIG. 8 is a plot representing the catalyst activity changes over time and differences thereof in oxidative dehydrogenation of n-butane between the magnesium o-vanadate catalyst supported by the magnesia-zirconia complex carrier according to the example 2 of the present invention and the magnesia-supported magnesium o-vanadate catalyst according to comparative example 3 prepared by the conventional technique, the comparative preparation example 3.

From the oxidative dehydration results obtained from the magnesia-supported magnesium o-vanadate catalyst and the magnesium o-vanadate catalyst supported by the magnesia-zirconia complex carrier, in order to observe the effect of the carrier used for a magnesium o-vanadate catalyst over time, each case of using magnesia and magnesia-zirconia carrier was subjected to the test as described in the above example 2 and the comparative example 3 and the results were compared, and the activity changes to the reaction over time during 24 hours were represented in the following Table 11 and FIG. 8.

TABLE 11

Reaction activity changes to the oxidative dehydrogenation of 3 species of magnesium o-vanadate catalysts based on a magnesium-supported magnesium o-vandate catalyst and magnesia-zirconia complex carrier over time

| | Yield of dehydrogenation product (%) | | | | | | | | | | | | | | | |
|---|---|---|---|---|---|---|---|---|---|---|---|---|---|---|---|---|
| | time (h) | | | | | | | | | | | | | | | |
| catalyst | 1 | 2 | 3 | 4 | 5 | 6 | 7 | 8 | 9 | 10 | 11 | 12 | 15 | 18 | 21 | 24 |
| VMgO/ZrO$_2$ | 11.5 | 11.6 | 11.4 | 11.5 | 11.4 | 11.7 | 11.5 | 11.6 | 11.5 | 11.5 | 11.6 | 11.4 | 11.5 | 11.6 | 11.5 | 11.5 |
| VMgO/MgZrO1 | 13.2 | 13.3 | 13.6 | 13.8 | 13.8 | 1.9 | 14.0 | 13.6 | 13.9 | 13.8 | 13.4 | 13.2 | 13.4 | 13.3 | 13.1 | 13.2 |
| VMgO/MgZrO2 | 13.4 | 13.7 | 13.7 | 13.9 | 13.7 | 13.8 | 13.8 | 13.8 | 14.0 | 13.4 | 13.6 | 13.8 | 13.2 | 13.3 | 13.4 | 13.8 |
| VMgO/MgZrO4 | 17.0 | 16.7 | 17.3 | 17.4 | 17.5 | 17.0 | 16.9 | 17.0 | 17.1 | 16.9 | 17.0 | 16.0 | 15.9 | 16.0 | 15.8 | 16.0 |
| VMgO/MgO | 24.3 | 23.7 | 23.2 | 23.1 | 23.0 | 22.3 | 22.1 | 22.3 | 21.9 | 22.0 | 14.9 | 14.2 | 7.6 | 2.0 | 1.7 | 1.7 |

From above Table 11 and FIG. 8, regarding the catalyst activity test carried out by using each catalyst, it cab be observed that all of the 3 species of magnesium o-vanadate catalysts supported by magnesia-zirconia complex carrier maintained the initial activity, unlike the magnesia-supported magnesium o-vanadate catalyst which showed a high initial activity but had sudden and rapid inactivation at a certain point, thereby hardly having an activity as a catalyst. Accordingly, it can be determined that a magnesia-zirconia complex carrier is more suitable as a carrier for a catalyst for the oxidative dehydrogenation of n-butane than a magnesia carrier. This is because that the magnesia-zirconia complex carrier takes advantages of each magnesia and zirconia and exerts synergic effects such as excellent initial activity and reaction stability by combining a magnesia-supported magnesium o-vanadate catalyst which has an advantage of high initial activity and a drawback such as rapid inactivation with a zirconia which can exert the effect such as excellent reaction stability. Therefore, it was confirmed that a novel catalyst having advantages both of excellent initial activity and reaction stability was successfully achieved.

What is claimed is:

1. A method for preparing a carrier for a catalyst for oxidative dehydrogenation of n-butane comprising the following steps:

(a) preparing each alcohol solution of zirconium and oxalic acid by dissolving the zirconium precursor and oxalic acid into an alcohol, respectively, wherein a molar ration of oxalic acid to zirconium being 2-5 to 1;
(b) synthesizing zirconia by mixing the alcohol solution of zirconium and the alcohol solution of oxalic acid prepared in the above step (a);
(c) obtaining zirconia used for the preparation of a magnesia-zirconia complex carrier by separating, drying and heating the solid component zirconia from the solution resulted from the above step (b);
(d) impregnating zirconia obtained from the above step (c) with an aqueous magnesium salt solution; and
(e) obtaining a magnesia-zirconia complex carrier for a catalyst for oxidative dehydrogenation of n-butane by drying and heating the product resulted from the above step (d).

2. The method according to claim 1, wherein the molar ratio of magnesia:zirconia in the magnesia-zirconia complex carrier obtained from the step (e) is 0.5-16:1.

3. The method according to claim 1, wherein the zirconium precursor is at least one selected from the group consisting of zirconium chloride, zirconium oxynitrate and zirconium oxychloride.

4. The method according to claim 1, wherein the mixing of the alcohol solution of zirconium and the alcohol solution of oxalic acid is carried out by stirring at 1-12 hours.

5. The method according to claim 1, wherein, in the step (c), drying is carried out at 50~200° C. for 3-24 hours, and heating is carried out at 350~800° C. for 1-12 hours.

* * * * *